US007544801B2

(12) United States Patent
Dobrovolny

(10) Patent No.: US 7,544,801 B2
(45) Date of Patent: Jun. 9, 2009

(54) METHOD OF MANUFACTURING OF 7-ETHYL-10-HYDROXYCAMPTOTHECIN

(75) Inventor: Petr Dobrovolny, Trebic (CZ)

(73) Assignee: Pliva-Lachema A.S., Brno (CZ)

( * ) Notice: Subject to any disclaimer, the term of this patent is extended or adjusted under 35 U.S.C. 154(b) by 0 days.

(21) Appl. No.: 10/582,650

(22) PCT Filed: Dec. 14, 2004

(86) PCT No.: PCT/CZ2004/000085

§ 371 (c)(1),
(2), (4) Date: Jun. 13, 2006

(87) PCT Pub. No.: WO2005/058910

PCT Pub. Date: Jun. 30, 2005

(65) Prior Publication Data

US 2007/0123552 A1    May 31, 2007

(30) Foreign Application Priority Data

Dec. 16, 2003  (CZ)  .......................... PV 2003-3442

(51) Int. Cl.
*C07D 491/22* (2006.01)
(52) U.S. Cl. ....................................................... 546/48
(58) Field of Classification Search .................... 546/48
See application file for complete search history.

(56) References Cited

U.S. PATENT DOCUMENTS

| | | | |
|---|---|---|---|
| 3,894,029 A | 7/1975 | Winterfeldt et al. |
| 4,031,098 A | 6/1977 | Sugasawa |
| 4,399,276 A | 8/1983 | Miyasaka et al. |
| 4,399,282 A | 8/1983 | Miyasaka et al. |
| 4,473,692 A | 9/1984 | Miyasaka et al. |
| 4,604,463 A | 8/1986 | Miyasaka et al. |
| 4,914,205 A | 4/1990 | Sawada et al. |
| 5,061,800 A | 10/1991 | Yaegashi et al. |
| 5,491,237 A | 2/1996 | Fang et al. |
| 5,602,141 A | 2/1997 | Bedeschi et al. |
| 5,734,056 A | 3/1998 | Burk et al. |
| 5,843,954 A | 12/1998 | Yaegashi et al. |
| 6,235,907 B1 | 5/2001 | Henegar et al. |
| 6,310,210 B1 | 10/2001 | Ogawa et al. |
| 6,403,569 B1 | 6/2002 | Achterrath |
| 6,444,820 B1 | 9/2002 | Henegar et al. |
| 6,743,918 B2 | 6/2004 | Yaegashi et al. |
| 6,794,370 B2 | 9/2004 | Achterrath |
| 7,126,000 B2 | 10/2006 | Ogawa et al. |
| 7,151,179 B2 | 12/2006 | Lin et al. |
| 2004/0235878 A1 | 11/2004 | Lin et al. |
| 2005/0272757 A1 | 12/2005 | Naidu |
| 2006/0199961 A1 | 9/2006 | Dobrovolny |

FOREIGN PATENT DOCUMENTS

| | | |
|---|---|---|
| EP | 74770 | 3/1983 |
| EP | 88642 | 9/1983 |
| EP | 51289 | 4/1986 |
| EP | 74256 | 11/1986 |
| EP | 154584 | 2/1988 |
| EP | 154583 | 9/1988 |
| WO | WO96/31513 | 10/1996 |
| WO | WO2004/100897 | 11/2004 |
| WO | WO2005/019223 | 3/2005 |
| WO | WO2005/058910 | 6/2005 |

OTHER PUBLICATIONS

"Combination of Irinotecan (CPT-11) and 5-Fluorouracil with an analysis of cellular determinants of drug activity," Pavillard et al., Biochemical Pharmacology, vol. 56: 1315-1322, 1998.

"Clinical advances with topoisomerase I inhibitors in gastrointestinal malignancies," Armand, Jean-Pierre et al., Anti-Cancer Drugs 10 (Suppl. 1): S5-S12 (1999).

"Phase I/II study of escalating dose of CPT-11 in combination with LV5FU2 ("De Gramont" regimen) every 2 weeks in the treatment of colorectal cancer (CRC) after 5-FU failure," Ducreux, M. et al., Abstract 823, Proc. of Amer. Soc. Clin. Oncol. 16:234a (1997).

"Phase I study of a weekly schedule of irinotecan (CPT-11), high-dose folinic acid (FA) and 5-fluorouracil (5-FU) as first line chemotherapy (CT) in metastatic colorectal cancer: Final results," Vanhoeffer, U. et al., Abstract 779, Proc. of Amer. Soc. Clin. Oncol. 17:202a (1998).

"Irinotecan (CPT-11) in the treatment of gastrointestinal cancers," Nishiyama, M., Japanese J. Chemotherapy 46(8):292-296 (1998).

(Continued)

*Primary Examiner*—Charanjit S Aulakh
(74) *Attorney, Agent, or Firm*—Foley & Lardner, LLP

(57) ABSTRACT

The method of manufacturing of 7-ethyl-10-hydroxycamptothecin of formula I characterized in that 7-ethyl-1,2,6,7-tetrahydrocampotothecin of formula IV is oxidized with an oxidizing agent selected from the group comprising iodosobenzene, an ester of iodosobenzene, sodium periodate, potassium periodate, potassium peroxodisulfate and ammonium peroxodisulfate, in a solvent formed by a saturated aliphatic monocarboxylic acid containing 1 to 3 carbon atoms, and in the presence of water.

15 Claims, No Drawings

OTHER PUBLICATIONS

"CPT-11 (Irinotecan) and 5-Fluorouracil: a Promising Combination for Therapy of Colorectal Cancer," Saltz, L. et al., European J. Cancer 32A(Suppl. 3):S24-S31 (1996).

"Phase I/II study of CPT-11 in combination with LV5FU2 (De Gramont-Regimen) every 2 weeks for the treatment of colorectal cancer (CRC) after 5-FU failure," Seitz, J.F. et al., Abstract 261, Annals of Oncology 9 (Suppl. 2):68 (1998).

"Phase I study of a weekly schedule of irinotecan (CPT-11) in combination with high-dose folinic acid and 5-fluorouracil as first line chemotherapy in patients with advanced colorectal cancer," Vanhoefer, U. et al., Abstract 967, Proc. of Amer. Soc. Clin. Oncol. 16:272a (1997).

"Synthesis and Antitumor Activity of 20(S)-Camptothecin Derivatives. A-Ring-Substituted 7-Ethylcamptothecins and their E-Ring-Modified Water-Soluble Derivatives," Yaegashi et al., Chemical & Pharmaceutical Bulletin. vol. 42. No. 12: 2518-2525 (1994).

"Chemical Modification of an Antitumor Camptothecin: Synthesis and Antitumor Activity of 7-C-Substituted Camptothecins," Sawada et al., Chemical & Pharmaceutical Bulletin. vol. 39. No. 10: 2574-2580 (1991).

"Synthesis and Antitumor Activity of A-Ring or E-Lactone Modified Water-Soluble Prodrugs of 20(S)-Camptothecin, Including Development of Irinotecan Hydrochloride Trihydrate," Sawada et al., Current Pharmaceutical Design, vol. 1 No. 1: 113-132 (1995).

Photodegradation reactions of CPT-II, a derivative of camptothecin. I: chemical structure of main degradation products in an aqueous solution, Akimoto et al., Drug Stability. vol. 1 No. 2.: 118-122.

"An Efficient Conversion of Camptothecin to 10-Hydroxycamptothecin," Wood et al., The Journal of Organic Chemistry, vol. 60. No. 17: 5739-5740 (1995).

"Synthesis and Antitumor Activity of 20(S)-Camptothecin Derivatives: Carbamate-Linked, Water-Soluble Derivatives of 7-Ethyl-10-hydroxycamptothecin," Sawada et al., Chemical & Pharmaceutical Bulletin, vol. 39. No. 6 1446-1454 (1991).

"Synthesis and Antitumor Activity of 20(S)-Camptothecin Derivatives: A-Ring Modified and 7, 10-Disubstituted Camptothecins," Sawada et al., Chemical & Pharmaceutical Bulletin, vol. 39. No. 12: 3183-3188 (1991).

METHOD OF MANUFACTURING OF 7-ETHYL-10-HYDROXYCAMPTOTHECIN

FIELD OF THE INVENTION

This invention relates to the method of manufacturing of 7-ethyl-10-hydroxycamptothecin of formula I

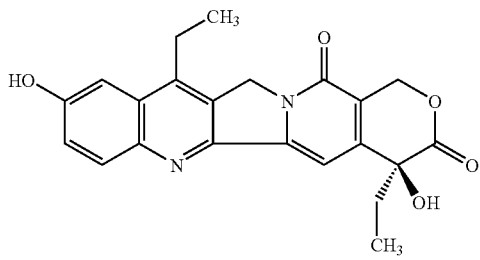

which is used for manufacturing of cytostatically active irinotecan hydrochloride trihydrate, effective particularly in treatment of lung and rectum cancer. The cytostatic effect of irinotecan hydrochloride trihydrate is based on its ability to inhibit topoisomerase.

BACKGROUND OF THE INVENTION

So far, 7-ethyl-10-hydroxycamptothecin is usually prepared in two reaction steps. In the first reaction step, 7-ethyl-camptothecin of formula II

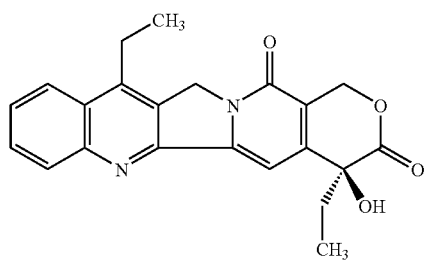

is oxidized with hydrogen peroxide in acetic acid under formation of 7-ethylcamptothecin 1-oxide of formula III

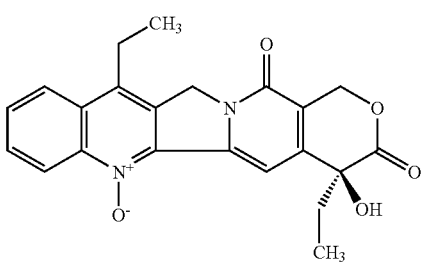

which in the second reaction step is dissolved-in the solvent system dioxane-acetonitrile-water and the solution is irradiated with UV light in the presence of sulfuric acid to afford the desired 7-ethyl-10-hydroxycamptothecin (see U.S. Pat. No. 4,473,692 and U.S. Pat. No. 4,513,138 and Zhongguo Yaowu Huaxue Zazhi 2001, 11 (4), 238-240).

However, this method of manufacturing of 7-ethyl-10-hydroxycamptothecin suffers from the fact that the oxidation of 7-ethylcamptothecin in the first reaction step requires relatively great amount of acetic acid (300 ml of acetic acid per 1 gram of 7-ethylcamptothecin). In the isolation of the obtained 7-ethylcamptothecin 1-oxide it is necessary to evaporate one fourth of the acetic acid volume, add water to the evaporation residue and subsequently collect the precipitated 7-ethylcamptothecin 1-oxide by filtration. This isolation procedure is demanding and affects very unfavourably the yield of 7-ethylcamptothecin 1-oxide. In the second step, the isolation of 7-ethyl-10-hydroxycamptothecin, consists in removal of the solvent mixture by distillation, dilution with water, extraction with chloroform and drying the chloroform layer over magnesium sulfate, followed by purification on a silica gel column with the aim to remove impurities arising in the UV irradiation. In spite of this complicated isolation procedure, the obtained 7-ethyl-10-hydroxycamptothecin still contains up to 22% by weight of 7-ethylcamptothecin. In this method the total yield of both reaction steps is only about 38%.

The aim of the invention is to find a less demanding method of producing 7-ethyl-10-hydroxycamptothecin that would afford 7-ethyl-10-hydroxycamptothecin in higher yields and higher purity. This aim has been achieved by the method according to the present invention.

SUMMARY OF THE INVENTION

The present invention relates to the method of manufacturing of 7-ethyl-10-hydroxycamptothecin of formula I

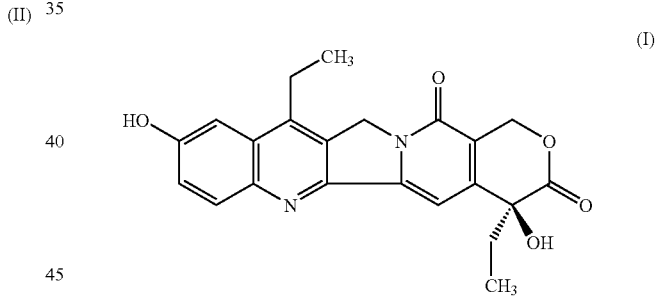

which is characterized in that 7-ethyl-1,2,6,7-tetrahydro-camptothecin of formula IV

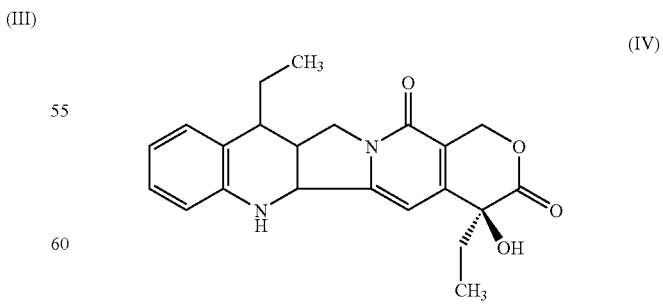

is oxidized with an oxidizing agent selected from the group comprising iodosobenzene, an ester of iodosobenzene, sodium periodate, potassium periodate, potassium peroxodisulfate and ammonium peroxodisulfate, in the presence of a solvent formed by a saturated aliphatic monocarboxylic acid comprising 1 to 3 carbon atoms, and in the presence of water.

The oxidizing agent is preferably an ester of iodosobenzene, more preferably an ester of iodosobenzene of general formula V

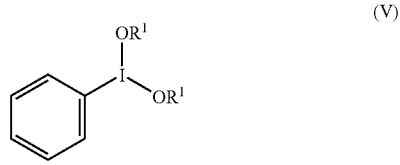

in which substituents $R^1$ are the same or different and designate hydrogen, —C(O)—$R^2$ or —SO$_2$—$R^3$ where $R^2$ and $R^3$ independently are selected from a group comprising an optionally substituted alkyl group having 1 to 6 carbon atoms, an optionally substituted cycloalkyl group having 3 to 8 carbon atoms, an optionally substituted aryl group having 6 to 12 carbon atoms, and an optionally substituted aralkyl group in which the aryl moiety has 6 to 12 carbon atoms and the alkyl moiety has 1 to 4 carbon atoms, with the proviso that at least one of the substituents $R^1$ is not the hydrogen atom, in particular an ester of iodosobenzene selected from a group comprising iodobenzene diacetate, iodobenzene bis(trifluoroacetate) and hydroxy(tosyloxy)iodobenzene. Iodobenzene diacetate is advantageously used in an amount of 0.99 to 1.85 mol, more advantageously 1.28 to 1.56 mol, per 1 mol of 7-ethyl-1,2,6,7-tetrahydrocamptothecin.

Suitable solvents include acetic acid, formic acid or trifluoroacetic acid. Preference is given to acetic acid in amounts from 668 to 1001 mol, more preferably 751 to 918 mol, per 1 mol of 7-ethyl-1,2,6,7-tetrahydrocamptothecin.

Water is advantageously used in amounts from 0.98 to 1.88 mol, preferably from 1.28 to 1.58 mol, per 1 mol of 7-ethyl-1,2,6,7-tetrahydrocamptothecin.

The oxidation is carried out preferably at a temperature in the range of 15 to 30° C., more preferably at 18 to 25° C., the reaction time being 5 to 30 minutes, more preferably 10 to 15 minutes.

The starting 7-ethyl-1,2,6,7-tetrahydrocamptothecin is preferably obtained by hydrogenation of 7-ethylcamptothecin of formula II

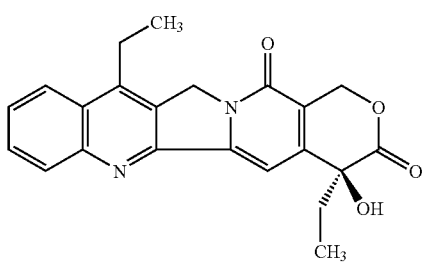

in a saturated aliphatic monocarboxylic acid having 1 to 3 carbon atoms, using hydrogen in the presence of a hydrogenation catalyst and a sulfur compound partly deactivating the hydrogenation catalyst.

Preferred saturated aliphatic monocarboxylic acids are formic acid, acetic acid or trifluoroacetic acid, more preferred being acetic acid in an amount of 791 to 1187 mol, most preferably 890 to 1088 mol, per 1 mol of 1-ethylcamptothecin.

Preferred sulfur compound that partly deactivates the hydrogenation catalyst is dimethyl sulfoxide, preferably in an amount of 0.18 to 0.33 mol, more preferably in an amount of 0.23 to 0.28 mol, per 1 mol of 7-ethylcamptothecin.

Preferred hydrogenation catalyst is a noble metal, preferably platinum which is advantageously used on a carrier consisting of an activated carbon or aluminum oxide. Platinum is advantageously used in an amount of 0.018 to 0.027 mol, more advantageously in an amount of 0.020 to 0.025 mol, per 1 mol of 7-ethylcamptothecin, in the form of hydrogenation catalyst consisting of platinum on an activated carbon with platinum content of 5%. The hydrogenation is performed advantageously at a pressure from 0.3 to 0.7 MPa, more preferably at 0.4 to 0.6 MPa, at a temperature from 45 to 85° C., more preferably at 58 to 72° C., for 24 to 70 hours, more preferably for 40 to 50 hours.

After the end of the oxidation, undesired compounds are removed in the following way. The solvent is distilled off, 7-ethyl-10-hydroxycamptothecin is precipitated in acetonitrile and isolated by filtration and washing with acetonitrile. In the procedure according to the present invention, at least 58% yield of 7-ethyl-10-hydroxycamptothecin is achieved in a relative purity of 90%, as determined by high performance liquid chromatography.

A substantial advantage of the method according to this invention over the prior art ones is that in the oxidation of 7-ethyl-1,2,6,7-tetrahydrocamptothecin no coloured side products are formed that need be removed by chromatography on a silica gel column. In an advantageous embodiment of this invention, the oxidation is preceded by hydrogenation of 7-ethylcamptothecin under formation of 7-ethyl-1,2,6,7-tetrahydrocamptothecin which advantageously is not isolated, the oxidation being performed directly with the obtained hydrogenation mixture from which only the hydrogenation catalyst has been removed.

In the following example, the method according to this invention is described in more detail, this example being for illustration only, without limiting in any way the scope of the invention which is unequivocally defined by the patent claims and the description part.

EXAMPLES

Example 1

In a 100 ml beaker, 0.5 g (1.239 mmol) of 7-ethylcamptothecin, 0.32 g of 5% hydrogenation catalyst Pt/C (containing 0.028 mmol of platinum) and 0.025 ml (0.352 mmol) of dimethyl sulfoxide are added to 70 ml of acetic acid. The obtained suspension is quantitatively transferred into a 100 ml autoclave. After closure, the autoclave is flushed three times with nitrogen at the pressure of 0.5 MPa and then three times with hydrogen at the pressure of 0.5 MPa. The temperature is adjusted to 65° C. and the mixture is stirred at 950 r.p.m. The hydrogen pressure is adjusted to 0.5 MPa. After 43.5 hours the consumption of hydrogen stops and the procedure is terminated. After cooling to 25° C., the stirring is stopped and the internal pressure is equilibrated with the ambient atmosphere. The autoclave is flushed three times with nitrogen, the hydrogenation catalyst is removed from the hydrogenation mixture by filtration under pressure of nitrogen and the catalyst cake is washed with 10 ml of acetic acid. The obtained solution (80 ml) of 7-ethyl-1,2,6,7-tetrahydrocamptothecin is immediately added under vigorous stirring into a 250 ml one-necked flask containing 22 ml (1.218 mol) of water and 0.77 g (2.343 mmol) of iodobenzene diacetate. The obtained solution is stirred for 15 minutes at 22° C. Then the solvent is evaporated and the residue is mixed with 10 ml of acetonitrile. The obtained suspension is homogenized by sonication. The solid 7-ethyl-10-hydroxycamptothecin is isolated by filtration, washed on the filter with 10 ml of acetonitrile and dried to the constant weight in a vacuum oven at 60° C. to 65° C. The yield of 7-ethyl-10-hydroxycamptothecin is 0.283 g (58.3%). Its relative purity, determined by high performance liquid chromatography, is 90.2%.

The invention claimed is:

1. A process for the preparation of 7-ethyl-10-hydroxy-camptothecin of formula I

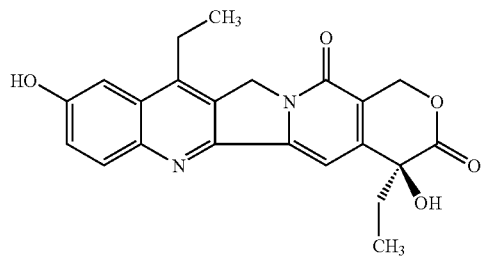

(I)

comprising oxidizing 7-ethyl-1,2,6,7-tetrahydrocamptothecin of formula IV

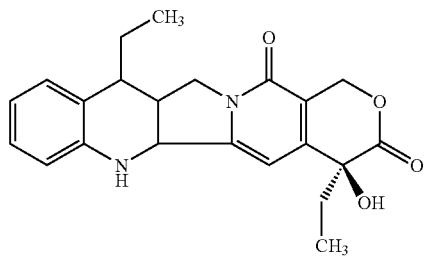

(IV)

with iodobenzene diacetate in acetic acid and water, wherein the amount of acetic acid is 668 to 1130 mol per 1 mol of 7-ethyl-1,2,6,7-tetrahydrocamptothecin, and the oxidation is carried out for 5 to 30 minutes.

2. The process according to claim 1, wherein the starting 7-ethyl-1,2,6,7-tetrahydrocamptothecin is obtained by hydrogenation of 7-ethylcamptothecin of formula II

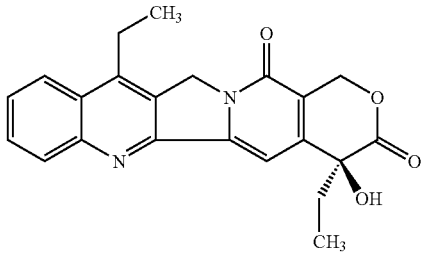

(II)

in a saturated aliphatic monocarboxylic acid having 1 to 3 carbon atoms, using hydrogen in the presence of a hydrogenation catalyst and a sulfur compound that partly deactivates the hydrogenation catalyst.

3. The process according to 2, wherein the saturated aliphatic acid is formic acid, acetic acid or trifluoroacetic acid.

4. The process according to claim 3, wherein acetic acid is used in an amount of 791 to 1187 mol per 1 mol of 7-ethyl-camptothecin.

5. The process according to claim 2, wherein the sulfur compound that partly deactivates the hydrogenation catalyst is dimethyl sulfoxide.

6. The process according to claim 5, wherein dimethyl sulfoxide is used in an amount 0.18 to 0.33 mol per 1 mol of 7-ethylcamptothecin.

7. The process according to claim 2, wherein the hydrogenation catalyst is a noble metal.

8. The process according to claim 7, wherein the noble metal is platinum.

9. The process according to claim 2, wherein the hydrogenation catalyst is platinum on an activated carbon or aluminum oxide carrier.

10. The process according to claim 9, wherein the platinum is used in an amount of 0.018 to 0.027 mol per 1 mol of 7-ethylcamptothecin, in the form of a hydrogenation catalyst, formed by platinum on an activated carbon with a platinum content 5%.

11. The process according to claim 2, wherein the hydrogenation is carried out at a pressure from 0.3 to 0.7 Mpa.

12. The process according to claim 11, wherein the hydrogenation is carried out at a temperature from 45 to 85° C.

13. The process according to claim 11, wherein the hydrogenation is carried out for 24 to 70 hours.

14. The process according to claim 1 wherein the amount of iodobenzene diacetate used is 0.99 mol to 1.9 mol per mol of 7-ethyl-1,2,6,7-tetrahydrocamptothecin.

15. The process according to claim 1 wherein the oxidation is carried out at a temperature ranging from 15 to 30° C.

* * * * *